(12) United States Patent
Ruan

(10) Patent No.: US 9,802,008 B2
(45) Date of Patent: Oct. 31, 2017

(54) DISPOSABLE PEN NEEDLE WITH RE-USE PREVENTION FEATURES

(71) Applicant: Becton, Dickinson and Company, Frankliln Lakes, NJ (US)

(72) Inventor: Tieming Ruan, Belmont, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 405 days.

(21) Appl. No.: 14/186,365

(22) Filed: Feb. 21, 2014

(65) Prior Publication Data

US 2014/0171904 A1    Jun. 19, 2014

Related U.S. Application Data

(63) Continuation of application No. 13/138,306, filed as application No. PCT/US2010/000305 on Feb. 4, 2010, now Pat. No. 8,764,706.

(60) Provisional application No. 61/150,671, filed on Feb. 6, 2009.

(51) Int. Cl.
*A61M 5/32* (2006.01)
*A61M 5/50* (2006.01)
*A61M 5/00* (2006.01)

(52) U.S. Cl.
CPC .......... *A61M 5/5086* (2013.01); *A61M 5/002* (2013.01); *A61M 2205/583* (2013.01)

(58) Field of Classification Search
CPC .. A61M 5/002; A61M 5/3202; A61M 5/3205; A61M 2205/583; A61M 5/5086
See application file for complete search history.

(56) References Cited

U.S. PATENT DOCUMENTS

| | | | | |
|---|---|---|---|---|
| 3,934,722 A | * | 1/1976 | Goldberg | B65D 41/32 206/365 |
| 4,300,678 A | * | 11/1981 | Gyure | A61M 5/002 206/364 |
| 4,623,336 A | | 11/1986 | Pedicano et al. | |
| 4,935,012 A | * | 6/1990 | Magre | A61B 5/1433 604/192 |
| 5,338,310 A | * | 8/1994 | Lewandowski | A61B 5/1438 604/110 |
| 5,971,966 A | | 10/1999 | Lav | |

(Continued)

FOREIGN PATENT DOCUMENTS

| | | |
|---|---|---|
| EP | 1 138 338 A1 | 4/2001 |
| JP | 07-148258 | 6/1995 |

(Continued)

OTHER PUBLICATIONS

Office Action Issued in Japanese Patent Application No. 2011-549156 dated Aug. 19, 2014.

(Continued)

*Primary Examiner* — Aarti B Berdichevsky
(74) *Attorney, Agent, or Firm* — Dickinson Wright PLLC

(57) ABSTRACT

A pen needle (521) for a drug delivery device (100) includes a hub (511) and a needle (502) fixedly connected to the hub (511). An outer cover (501) removably receives the hub (511) and the needle (502). A locking member (505) locks the hub (511) and the needle (502) in the outer cover (501). The hub (625) may have a colored portion (629) visible to the user to indicate that the needle (623) has been used.

15 Claims, 14 Drawing Sheets

(56) References Cited

U.S. PATENT DOCUMENTS

| | | | |
|---|---|---|---|
| 7,553,293 B2* | 6/2009 | Jensen | A61M 5/326 604/110 |
| 7,665,605 B2 | 2/2010 | Erickson et al. | |
| 2002/0004648 A1 | 1/2002 | Larsen et al. | |
| 2004/0054336 A1 | 3/2004 | Klint et al. | |
| 2005/0107740 A1 | 5/2005 | Jensen et al. | |
| 2005/0267416 A1 | 12/2005 | Mohammed | |
| 2006/0229562 A1 | 10/2006 | Marsh et al. | |
| 2007/0149924 A1 | 6/2007 | Marsh | |
| 2008/0015519 A1 | 1/2008 | Klint | |
| 2008/0262421 A1 | 10/2008 | Schraga | |
| 2009/0005742 A1 | 1/2009 | Liversidge | |
| 2009/0069753 A1 | 3/2009 | Ruan et al. | |
| 2012/0016300 A1 | 1/2012 | Ruan | |

FOREIGN PATENT DOCUMENTS

| | | |
|---|---|---|
| JP | 11-137687 | 5/1999 |
| WO | WO 9602290 A1 | 2/1996 |
| WO | 01/23021 A1 | 4/2001 |
| WO | WO 2010/090735 | 8/2010 |

OTHER PUBLICATIONS

Office Action Issued in Japanese Patent Application No. 2011-549156 dated Nov. 26, 2013.

* cited by examiner

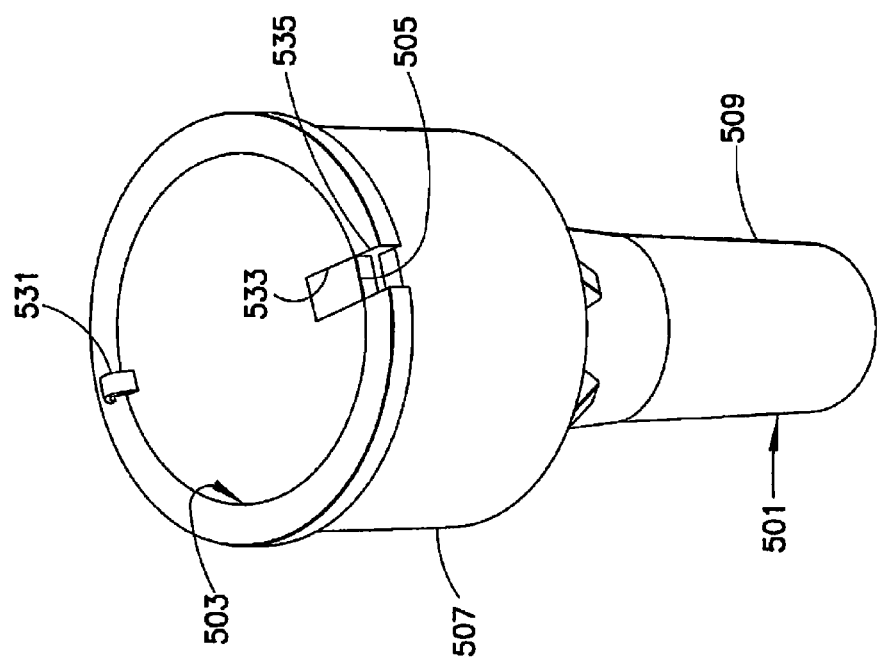
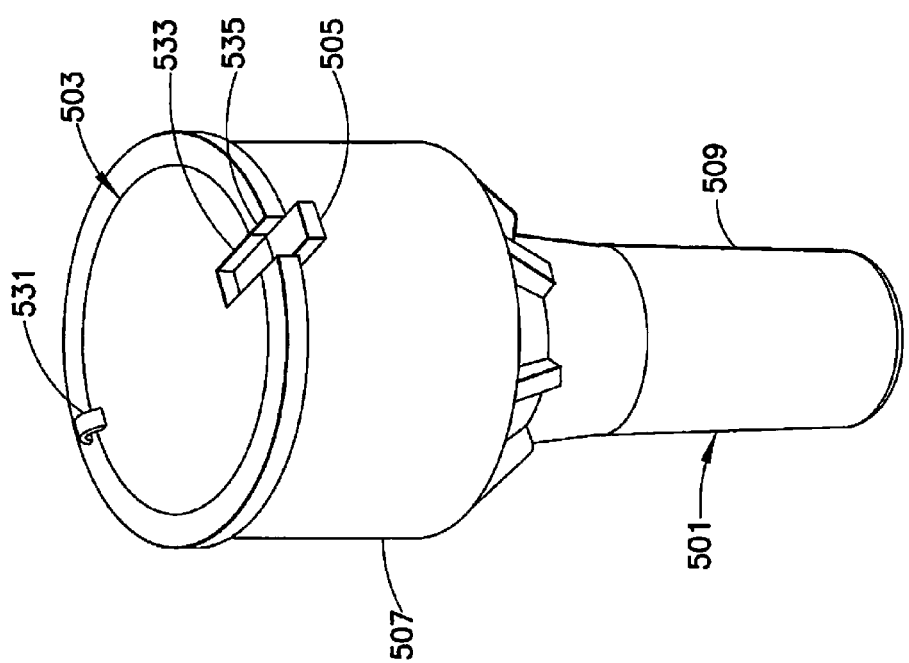

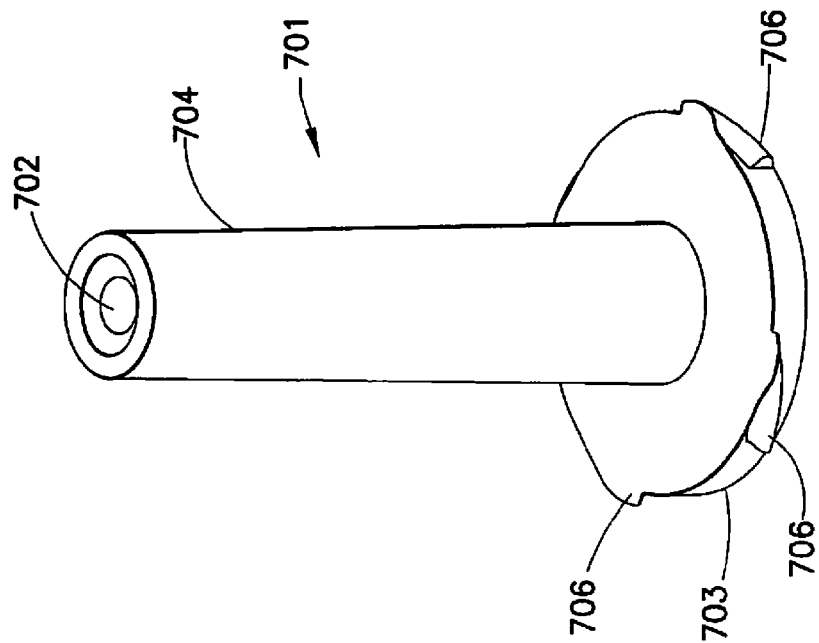
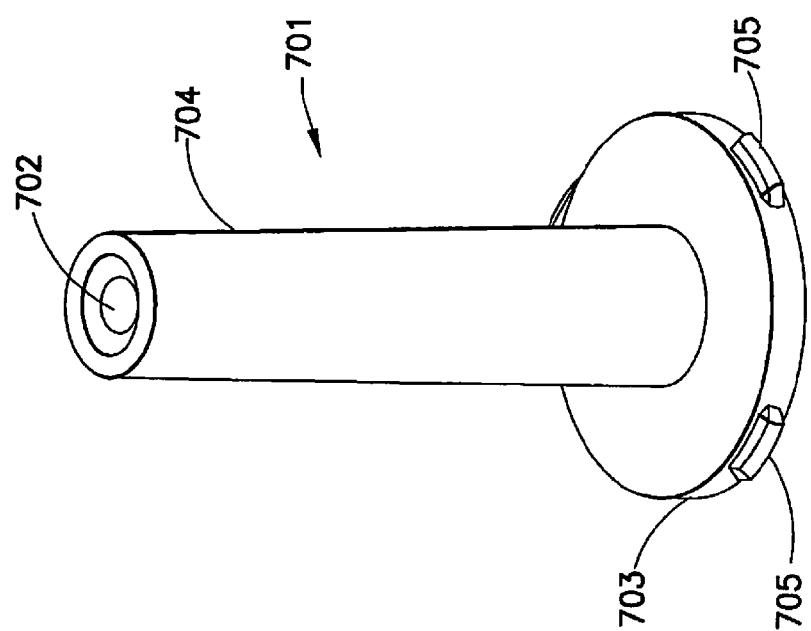

DISPOSABLE PEN NEEDLE WITH RE-USE PREVENTION FEATURES

This application is a continuation of U.S. application Ser. No. 13/138,306, filed Oct. 10, 2011, which was the national stage of International Application No. PCT/US10/00305, filed Feb. 4, 2010, which claims the benefit under 35 U.S.C. §119(e) of U.S. Provisional Application Ser. No. 61/150,671, filed Feb. 6, 2009, the entire contents of all of said prior applications being hereby incorporated by reference.

FIELD OF THE INVENTION

The present invention relates generally to a disposable pen needle with re-use prevention features. More particularly, the present invention relates to a disposable pen needle in which a cap of an outer cover has a tab that is connectable to the cap to prevent reuse of the pen needle. The present invention also relates to a pen needle that is lockable within an outer cover to prevent reuse of the pen needle.

BACKGROUND OF THE INVENTION

Insulin and other injectable medications are commonly given with drug delivery pens, whereby a disposable pen needle is attached to facilitate drug container access and allow fluid egress from the container through the needle into the patient.

As technology and competition advance, driving the desire for shorter, thinner, less painful, and more efficacious injections, the design of the pen needle and parts thereof becomes more and more important. Designs need to proactively address ergonomically improving injection technique, injection depth control and accuracy, the ability to be safely used and transported to disposal, and protection against misuse while maintaining the ability to be economically manufactured on a mass production scale.

Drug delivery devices, such as the exemplary drug delivery pen 100 shown in FIGS. 1 and 2, can be designed for subcutaneous, as well as intradermal, injections and typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the drug delivery pen 100 in a shirt pocket, purse or other suitable location and provide cover/protection from accidental needle injury.

FIG. 2 is an exploded view of the drug delivery pen 100 of FIG. 1. The dose knob/button 24 has a dual purpose and is used both to set the dosage of the medication to be injected and to inject the dosed medicament via the leadscrew 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the steel needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used, such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle by any suitable means, such as an interference fit or a snap fit. The outer cover 69 and the inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

An exploded perspective view of a pen needle 2 of an exemplary drug delivery pen is shown in FIG. 3. The pen needle 2 includes the cover (outer shield) 69, an inner shield 59, a needle cannula 11, and a hub 20. A proximal end 310 of the needle cannula 11 is inserted into a center opening in the distal (patient) end 405 of the hub 20 until a predetermined length of the distal (patient) end 305 of the needle cannula 11 remains extended. The needle cannula 11 is secured by epoxy or adhesive in the distal end 405 of the hub 20 within the hub protrusion 420.

To protect users from injury and the needle cannula 11 from being damaged, the inner shield 59 covers the exposed portion of the needle cannula 11. The open proximal end 210 of the inner shield 59 is placed over the exposed portion of the needle cannula 11. The open proximal end 110 of the cover 69 envelops the inner shield 59, needle cannula 11, and hub 20.

The distal end 105 of the cover 69 is closed to prevent contamination and damage to the inner components of pen needle 2, and to prevent injury to anyone who may handle it prior to use. The proximal end 410 of the hub 20 is typically covered by a sanitary paper or foil cover (not shown) glued on an end 110 of the cover 69. The drug delivery pen is then ready for shipment to a user. When the user is ready to use the drug delivery pen, the sanitary cover (not shown) is removed from the cover 69, the hub 20 is screwed onto a lower housing 17 of a standard pen 100 (FIGS. 1 and 2), and the cover 69 and shield 59 are separately removed from the hub 20/cannula 11 subassembly by a pulling action. The distal end 205 of the inner shield 59 is closed to cover the distal end 305 of the needle cannula 11 after the cover 69 is removed to protect the user from an accidental needle stick. The inner shield 59 is then removed to access the needle cannula 11. Thus, two separate pulling actions are required to remove both the cover 69 and the shield 59.

Many existing replacement needle assemblies include an inner shield and outer cover. The outer cover typically has a sanitary paper or foil seal that a user must remove to connect the pen needle to the cartridge of the pen assembly. However, the sanitary seal can be difficult to grasp and remove from the pen needle. Furthermore, once the sanitary seal is removed from the pen needle, nothing prevents a used pen needle that has been removed from a pen cartridge from being reused. Moreover, without the sanitary seal, nothing prevents a user from being accidentally stuck by the uncovered needle. Thus, a need exists for a pen needle that is easy to use and prevents reuse.

Another existing problem with pen needles is that there is no means to easily determine whether the pen needle has been previously used. Thus, a need exists for a pen needle that locks the pen needle in an outer cover to prevent reuse. A need also exists for a pen needle that has a color indicator to indicate that the pen needle has been previously used.

Existing drug delivery pens are disclosed in U.S. Patent Application Publication Nos. 2006/0229562 to Marsh et al., published on Oct. 12, 2006, and 2007/0149924 to R. Marsh, published on Jun. 28, 2007, the entire contents of both of which are hereby incorporated by reference.

Accordingly, a need exists for a disposable pen needle having an outer cover including a cap having a tab that is connectable to the cap to prevent reuse of the pen needle and to provide an easy to use pen needle.

SUMMARY OF THE INVENTION

In accordance with an aspect of the present invention, a need exists for a pen needle that is lockable within the outer cover to prevent reuse.

In accordance with another aspect of the present invention, a cap of an outer cover of a pen needle has a tab that protrudes outwardly from the outer cover to provide a cap that is easily opened to provide access to the pen needle.

In accordance with another aspect of the present invention, the tab is securable to the cap to lock the cap to the outer cover, thereby preventing reuse of a used pen needle and preventing accidental needle sticks from the used pen needle.

In accordance with another aspect of the present invention, a need exists for a pen needle that has a color indicator to clearly indicate whether the pen needle has been used.

The foregoing objects are basically attained by providing a pen needle for a drug delivery device that includes a hub and a needle fixedly connected to the hub. An outer cover removably receives the hub and the needle. A locking member locks the hub and the needle in the outer cover.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which:

FIG. 10 is a perspective view of the outer cover and cap of the pen needle of FIG. 4 with an unlocked tab;

FIG. 11 is a perspective view of the outer cover and cap of the pen needle of FIG. 9 with a locked tab;

FIGS. 18 and 19 are perspective views of a threaded inner shield according to another exemplary embodiment of the present invention;

Throughout the drawings, like reference numbers will be understood to refer to like parts, components and structures.

DETAILED DESCRIPTION OF THE EXEMPLARY EMBODIMENTS

Figure 1:
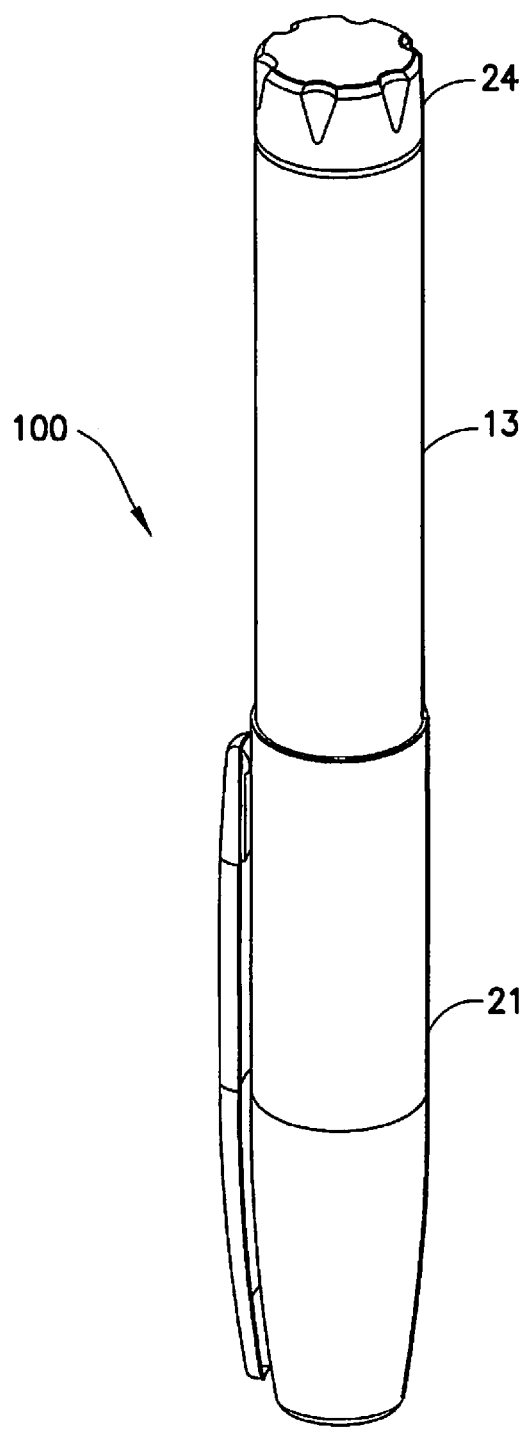
FIG. 1 is a perspective view of an assembled drug delivery pen.
Figure 2:
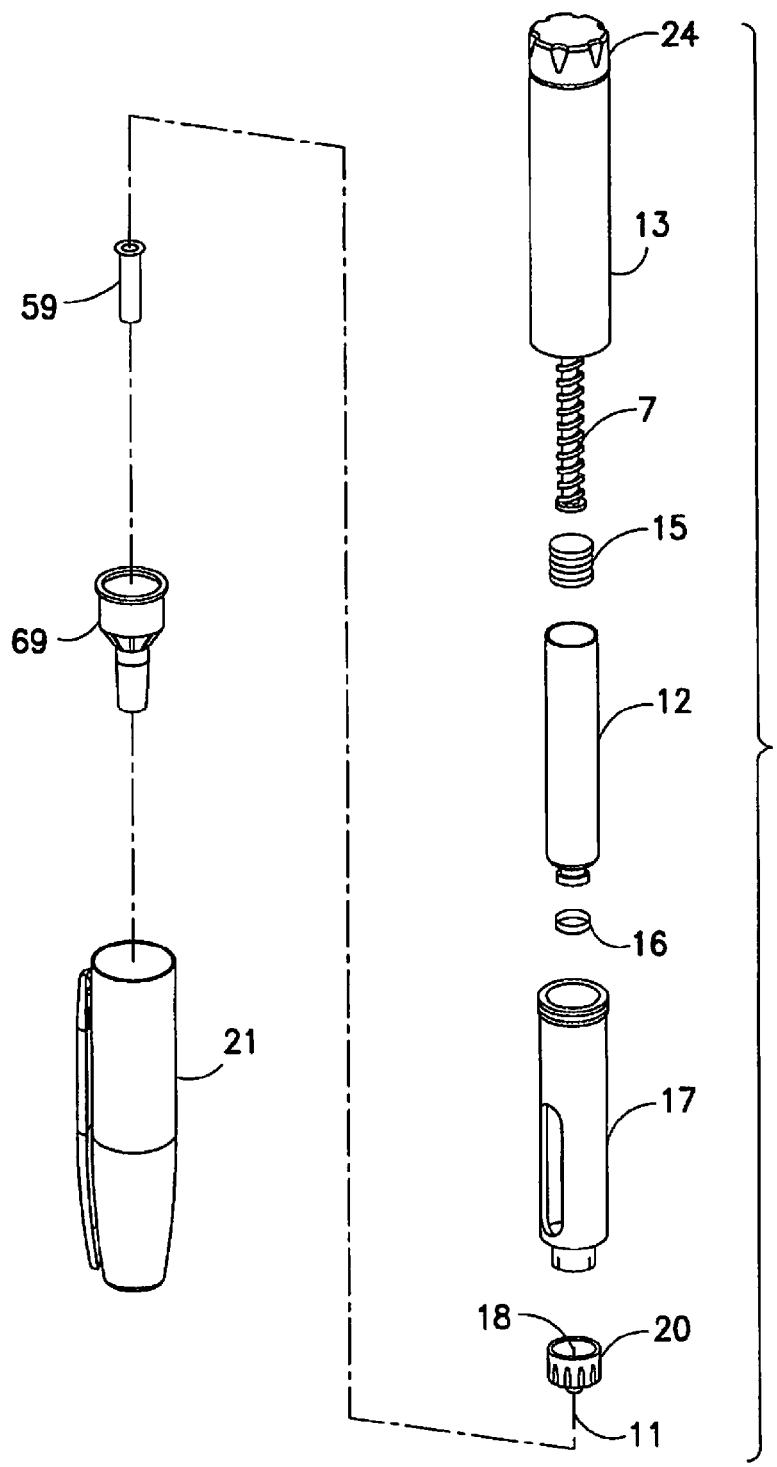
FIG. 2 is an exploded perspective view of the drug delivery pen of FIG. 1.
Figure 3:
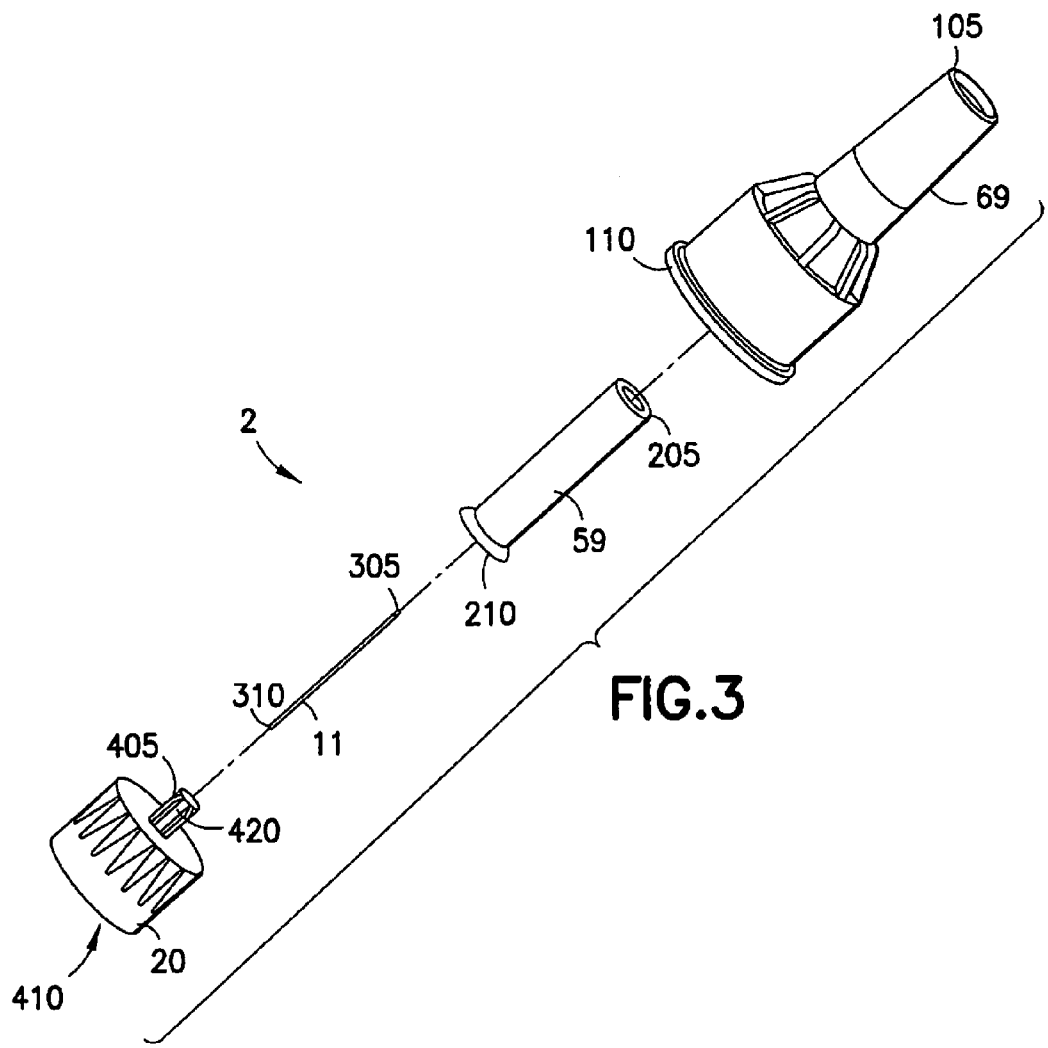
FIG. 3 is an exploded perspective view of a pen needle of the drug delivery pen of FIGS. 1 and 2.

The following description and details of exemplary embodiments of the present invention, while generally disclosed in a typical drug delivery pen, as shown in FIGS. 1-3, could more broadly apply to a needle and hub assembly for use in conjunction with, or incorporated onto, other injection devices such as syringes, autoinjectors and infusion devices.

In an exemplary embodiment of the present invention shown in FIGS. 4-9, an outer cover 501 is connected to a hub 511 of a pen needle 521, such as by a friction fit. The hub 511 has a needle 502 rigidly fixed thereto. A rigid plastic cap 503 is connected to the outer cover 501, such as by a living hinge 531. Preferably, the living hinge is formed during molding of the outer cover 501. Alternatively, the cap 503 may be snap fitted to the outer cover 501. The cap 503 has an integral, outwardly extending tab 505 to allow the user to grasp the tab easily, thereby facilitating opening of the cap by a user.

The outer cover 501 has a substantially cylindrical body 507. The cap 503 is connected to a first end of the body 507. An inwardly tapering body portion 508 is connected to a second end of the body 507. A projection 509 extends outwardly from the tapered body portion 507 in a direction away from the cap 503. The projection 509 is adapted to receive the needle 502 of the hub 511.

The cap 503 is preferably substantially circular, as shown in FIGS. 10 and 11. However, the tab 505 may be any suitable shape. The tab 505 is shaped to allow the user to grasp or engage the tab 505 more easily to facilitate opening and closing the cap 503. The cap 503 has a recess 533 and the outer cover 501 has a recess 535 through which the tab 505 extends, as shown in FIG. 10, prior to the tab being locked to the cap.

Figure 5:
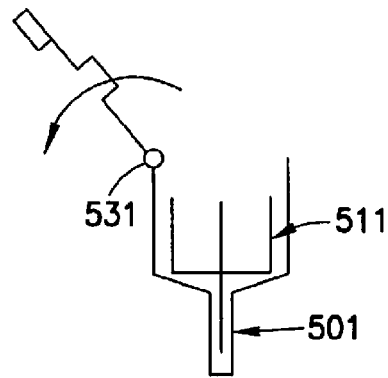
FIG. 5 is an elevational view of the outer cover in which the cap is opened to provide access to the pen needle.
Figure 8:
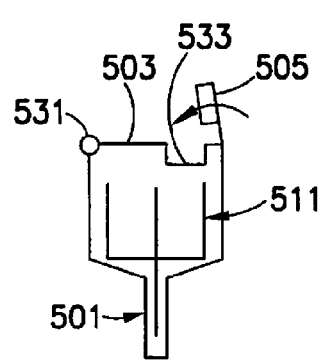
FIG. 8 is an elevational view of the outer cover in which the cap is closed and the tab is being moved to a locked position.
Figure 9:
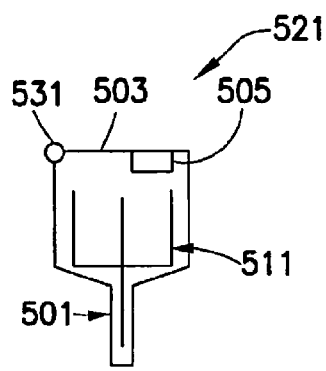
FIG. 9 is an elevational view of the outer cover in which the tab is locked to the cap of the outer cover.

To lock the tab 505 to the cap 503, the tab is moved into the recess 533 in the cap, thereby preventing the cap from being removed from the outer cover 501. The tab 505 may be connected to the cap in any suitable manner that allows the tab to be disposed in the cap recess 533. The tab may be initially rigidly attached to the cap 503 by a weakened line. The tab 505 is pushed upwardly by a user's finger to open the cap, as shown in FIG. 5. After the needle 502 is used and disposed in the outer cover 501, the cap 503 is held closed while the tab 505 is pivoted, or broken, at the line and secured within the recess 533, as shown in FIGS. 8 and 9. The tab 505 may be slightly larger than the cap recess 533 such that disposing the tab 505 in the recess 533 causes the cap 503 to expand to more securely secure the cap to the outer cover 501.

Figure 4:
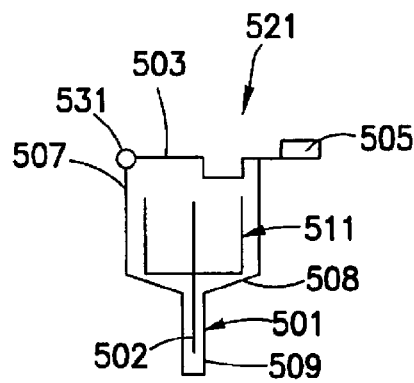
FIG. 4 is an elevational view of an outer cover for a pen needle having a tab connected to the cap, and the cap being connected to the outer cover according to an exemplary embodiment of the present invention.
Figure 6:
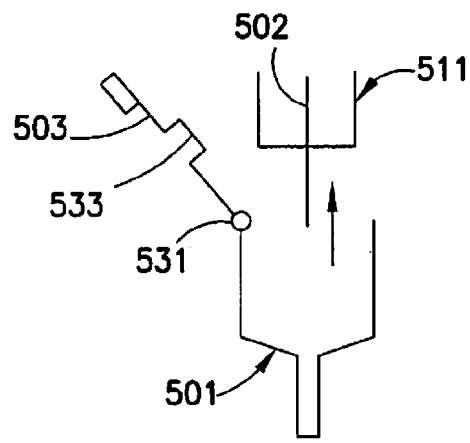
FIG. 6 is an elevational view of the outer cover in which the outer cover is separated from the pen needle to connect the pen needle to a cartridge.
Figure 7:
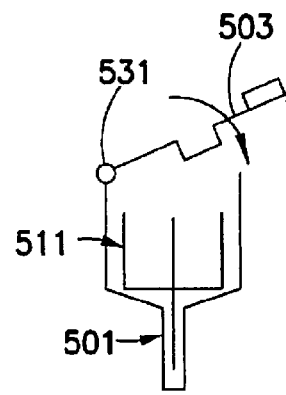
FIG. 7 is an elevational view of the outer cover in which a used pen needle has been separated from the cartridge and is received by the outer cover.

As shown in FIG. 4, prior to use of the pen needle 521, the cap 503 is sealed to the outer cover 501, thereby covering both ends of the needle 502 to maintain sterility and prevent an accidental needle stick. When the pen needle 521 is ready to be used, the cap 503 is opened to provide access to the hub 511 and needle 502, as shown in FIG. 5. The hub 511 is then connected to a lower housing 17 of a pen (FIG. 2) and the outer cover 501 is separated from the hub 511 and needle 502, as shown in FIG. 6. Once the needle 502 has been used, the hub 511 and needle 502 are separated from the lower housing 17 of the drug delivery device 100 (FIG. 1), reinserted in the outer cover 501 and the cap 503 is closed, as shown in FIG. 7. The cap 503 preferably creates an interference fit with the outer cover 501 to secure the cap to the outer cover. The tab 505 is then moved to a locked position, as shown in FIG. 8. Once the tab 505 is locked to the cap 503, as shown in FIGS. 9 and 11, the cap is prevented from being opened such that the pen needle 521 cannot be reused. Additionally, by locking the hub 511 within the outer cover 501 both ends of the used needle 502 are covered, thereby preventing a user from being accidentally stuck by the needle.

Because the tab 505 is locked to the cap 503 by the user, the pen needle 521 may be reused as often as desired, which is suitable for personal use, or used only once, which is suitable for hospital or professional use, before locking the tab to the cap. In a professional setting, such as in a hospital, locking the tab 505 to the cap 503 prevents reuse of the pen needle 521, thereby preventing blood cross-contamination between patients. Furthermore, when the tab 505 is locked to the cap 503, the non-patient end of the needle 502 is also covered, thereby preventing accidental needle sticks.

In another exemplary embodiment of the present invention, as shown in FIGS. 12-17, a hub and needle of a pen needle 621 are lockable within an outer cover 601.

Figure 12:
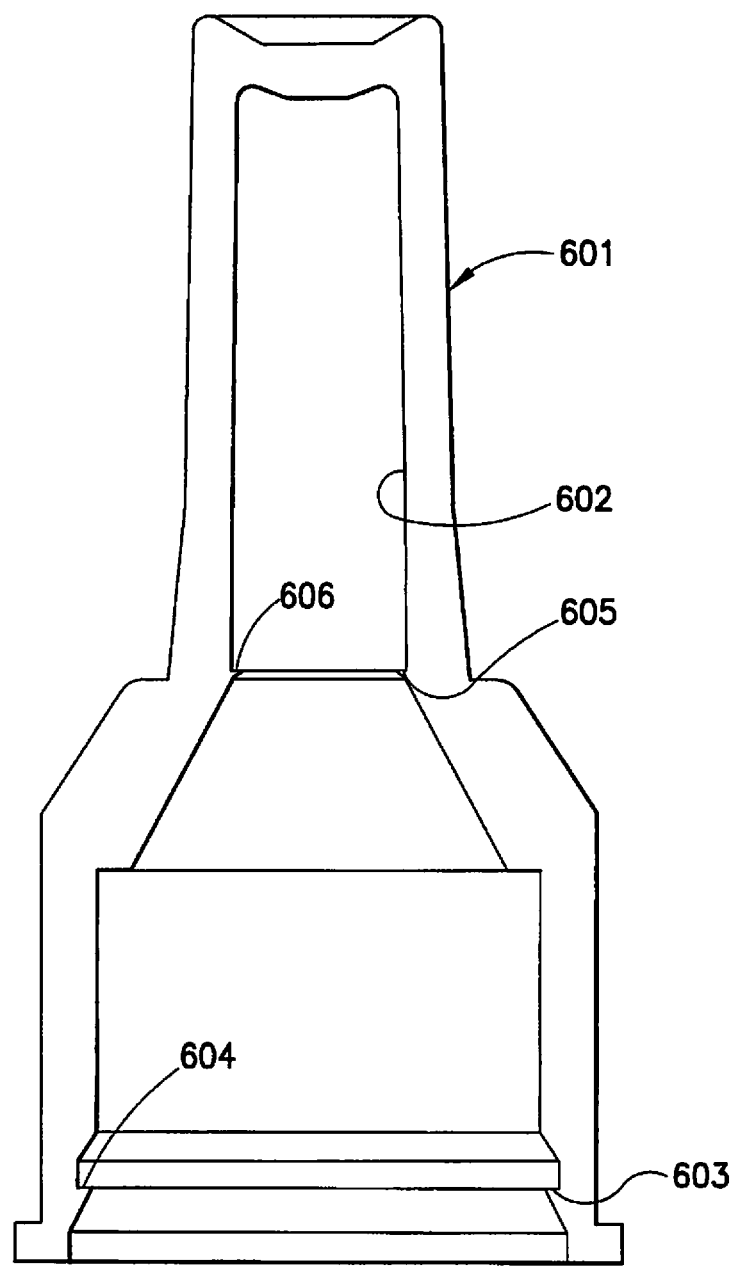
FIG. 12 is an elevational view in cross section of an outer cover according to another exemplary embodiment of the present invention.
Figure 15:
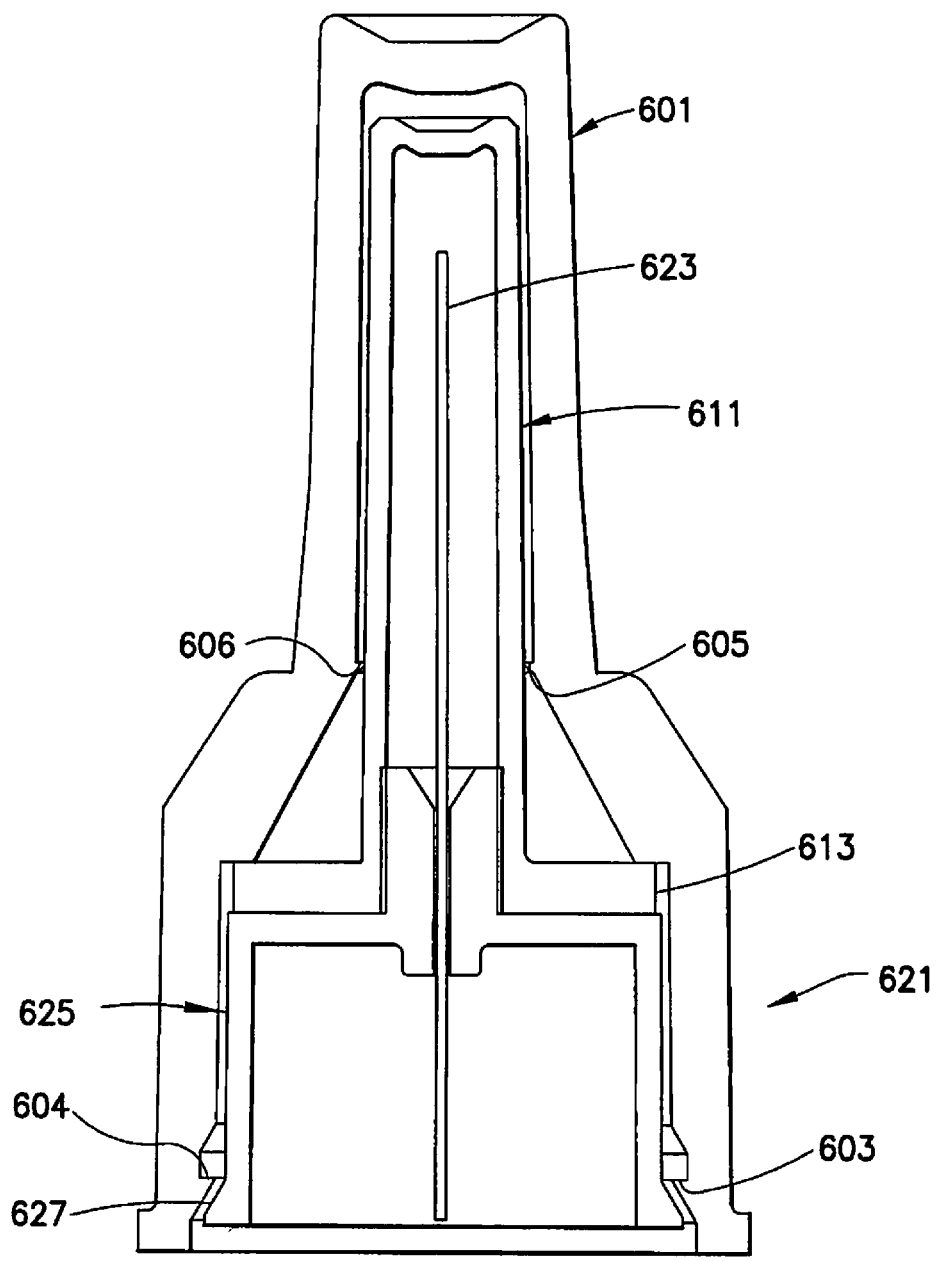
FIG. 15 is an elevational view in partial cross section of an assembled pen needle assembly of FIGS. 12-14 in which the inner shield is connected to the hub.

The outer cover 601, as shown in FIG. 12, has a first undercut 603 formed in an inner surface 602 and is adapted to receive the hub 625. The first undercut 603 forms a first flexible member 604 that prevents removal of the inserted hub 625. Preferably, the first flexible member 604 extends entirely around the circumference of the inner surface 602. The outer cover 601 also has a second undercut 605 formed in the inner surface 602 and is adapted to secure an inner shield 611 within the outer cover. The second undercut forms a second flexible member 606 that prevents removal of the inserted inner shield 611. Preferably, the second flexible 606 member extends entirely around the circumference of the inner surface 602. The second flexible member 606 engages an outer surface 614 of the projection 615 of the inner shield 611, thereby facilitating reception of the inner shield as shown in FIG. 15. The outer cover 601 is preferably clear and is preferably made of polypropylene.

Figure 13:
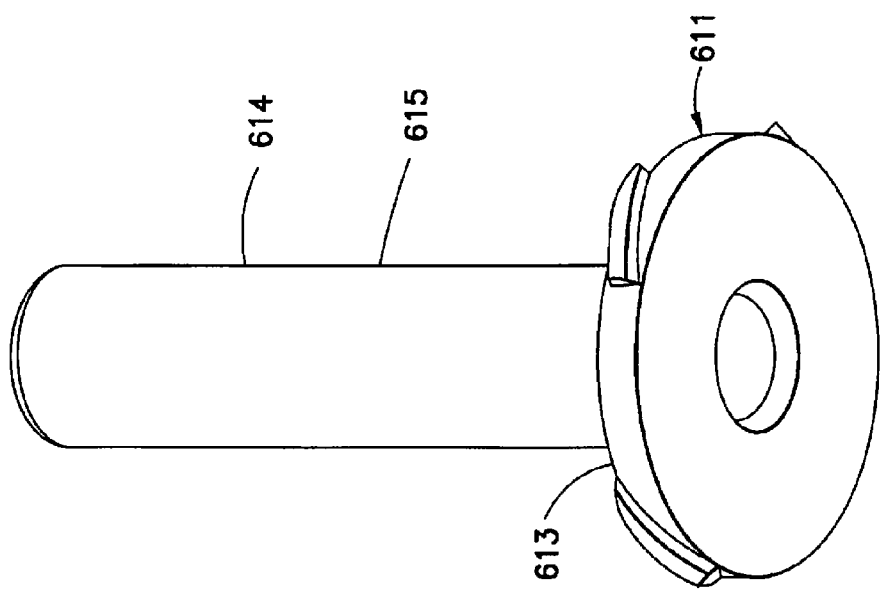
FIG. 13 is a perspective view of an inner shield according to another exemplary embodiment of the present invention.

The inner shield 611, as shown in FIG. 13, has a base 613 and a projection 615 extending from the base adapted to cover a needle 623, as shown in FIG. 15. The base 613 of the inner shield 611 has a larger and thicker base that reduces the likelihood of an accidental needle stick when a user attempts to dispose the inner shield over the needle 623 onto the hub 625. The projection 615 of the inner shield 611 is adapted to be received by the second undercut 605 of the outer cover 601.

Figure 14:
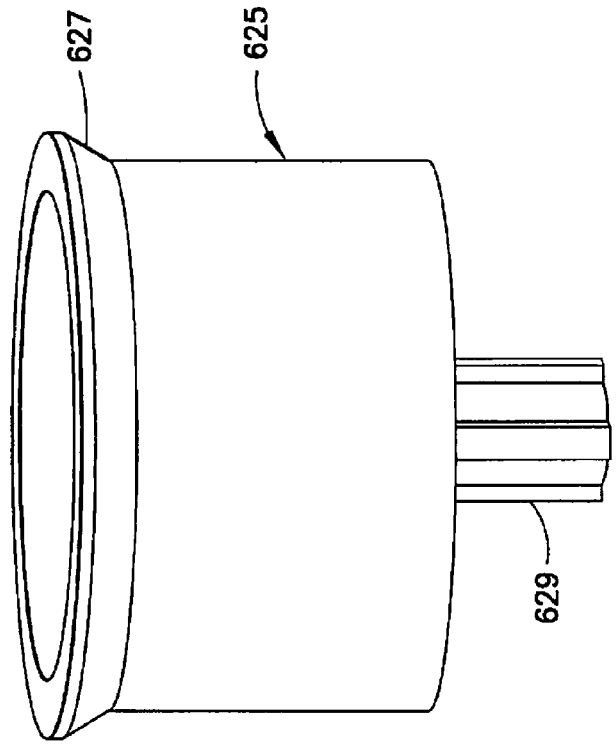
FIG. 14 is a perspective view of a hub according to another exemplary embodiment of the present invention.
Figure 16:
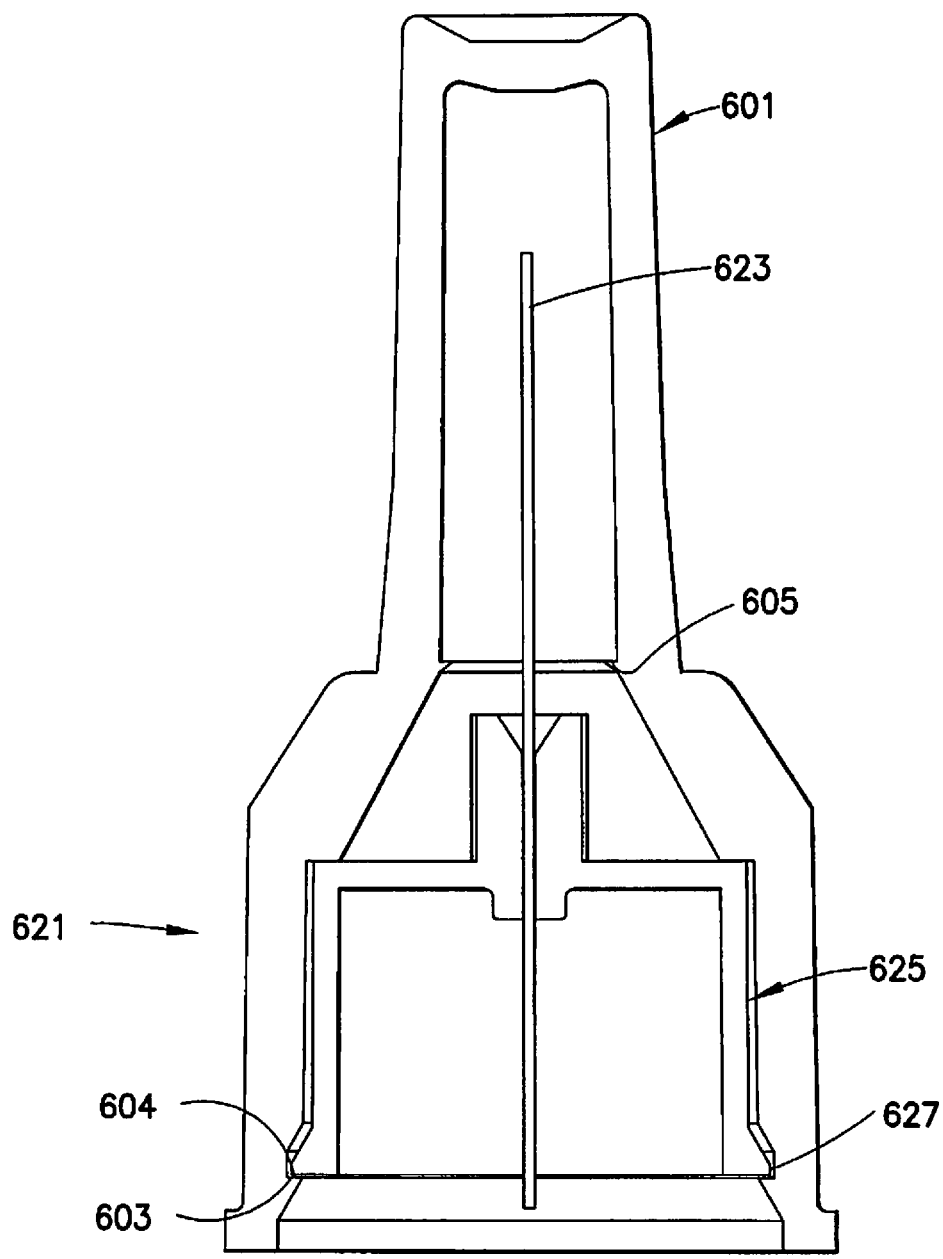
FIG. 16 is an elevational view in partial cross section of an assembled pen needle assembly of FIGS. 12-14 in which the hub is locked to the outer cover.

The hub 625 of the pen needle 621, as shown in FIG. 14, has a chamfered flange 627 adapted to be received by the first undercut 603 in the outer cover 601, as shown in FIG. 16. The hub 625 is preferably made of polypropylene.

FIG. 15 shows the pen needle 621 and inner shield 611 disposed within the outer cover 601 before use. The thickness of the base 613 of the inner shield 611 prevents the chamfered flange 627 of the hub 625 from being received beyond the first flexible member 604 formed by the first undercut 603 of the outer cover 601. After the needle 623 of the pen needle 621 is used to administer medication and the hub 625 is still connected to the lower housing 17 of the drug delivery device 100 (FIGS. 1 and 2), the outer cover 601 is disposed over the hub 625 and needle 623 of the pen needle 621, as shown in FIG. 16. Because the inner shield 611 is not disposed on the hub 625 of the pen needle 621, the chamfered flange 627 of the hub 625 is now received by first flexible member 604 formed by the first undercut 603 of the outer cover 601, as shown in FIG. 16. The chamfered flange 627 flexes the first flexible member 604 inwardly, thereby allowing the chamfered flange to move past the first flexible member. The chamfered flange 627 sits on the first flexible member 604, which is prevented from flexing downwardly. Thus, the chamfered flange 627 is locked within the outer cover 601 by the first flexible member 604, and the pen needle 621 may be removed from the lower housing 17 of the drug delivery device 100.

Figure 17:
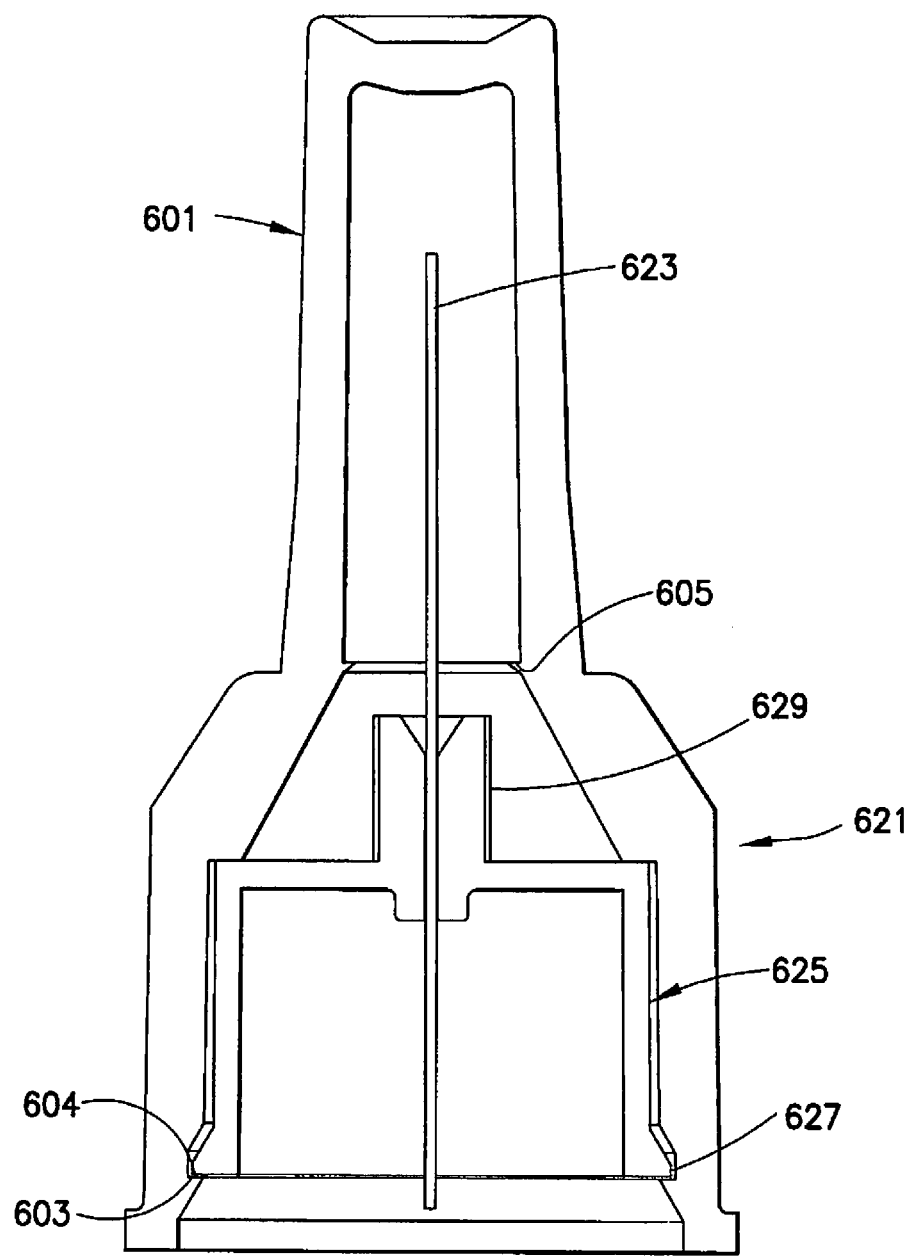
FIG. 17 is an elevational view in partial cross section of an assembled pen needle assembly of FIGS. 12-14 in which the hub is locked to the outer cover and the hub has a color indicator.

In a preferred embodiment of the present invention, the glue well 629 of the hub 625 of the pen needle 621 is molded or painted a predetermined color, such as red, to indicate that the pen needle has been used, as shown in FIG. 17. As shown in FIG. 15, the opaque inner shield 611 covers the glue well of the hub 625 such that the glue well is not visible to a user when the inner shield is disposed on the hub 625 to cover the needle 623. After the pen needle 621 has been used and the chamfered flange 627 is received by the first flexible member 604 formed by the first undercut 603 in the outer cover 601, the glue well 629 is visible through the clear cover 601 because it is no longer being covered by the inner shield 611, as shown in FIG. 17. The visibility of the colored glue well 629 indicates that the needle 623 of the pen needle 621 has been used. Accordingly, if the used pen needle is accidentally picked up by another user, the visibility of the colored glue well 629 through the outer cover 601 indicates that the needle 623 of the pen needle 621 has been used and should be properly discarded.

Figure 20:
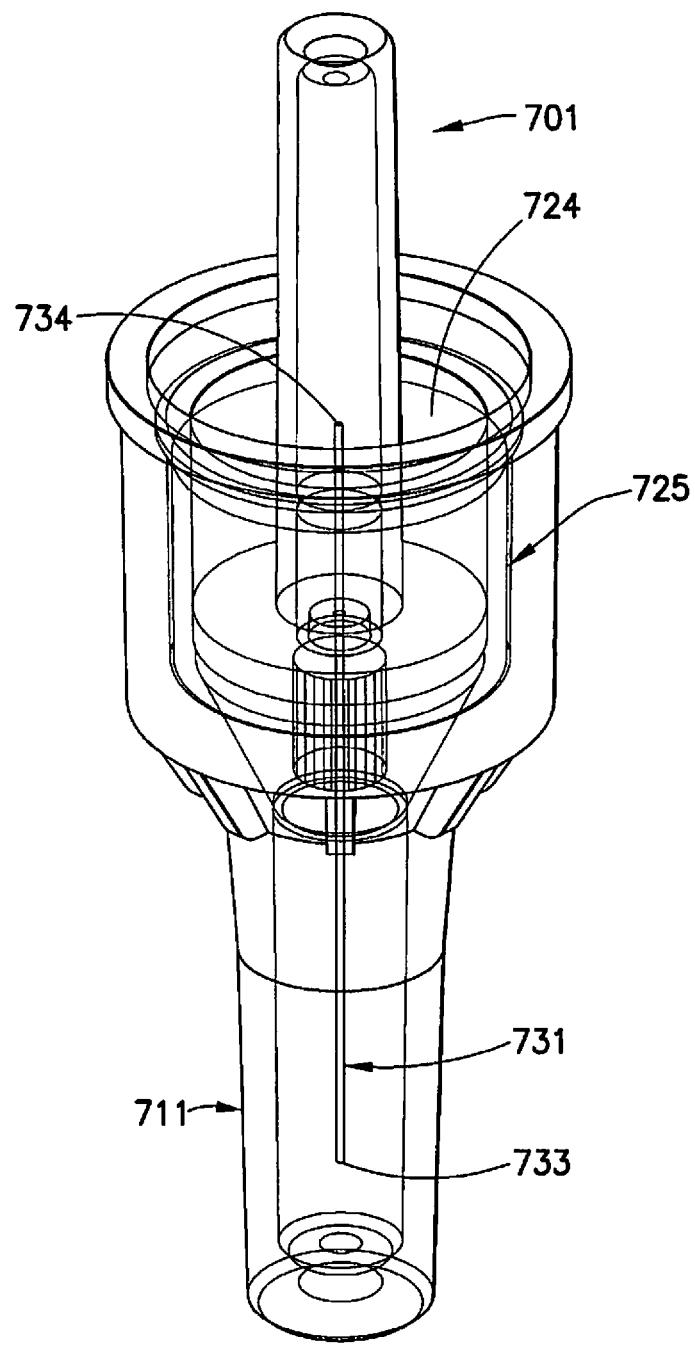
FIG. 20 is a perspective view of an inner shield of FIG. 18 or 19 threadably engaged with a needle hub to shield a non-patient end of a needle.

The outer cover 601 may have the cap and locking tab of the exemplary embodiment shown in FIGS. 4-11 to cover the non-patient end of the needle 623 that is exposed when the hub 625 is locked to the outer cover 601. Alternatively, an inner shield 701 may have threads 705 (FIG. 18) or 706 (FIG. 19) on a base 703 that threadably engage threads (by way of example, see FIG. 23) on an inner surface 724 of the hub 725, as shown in FIG. 20. Thus, when the hub 725 is locked to the outer cover 711, the outer cover 711 covers the patient end 733 of the needle 731 and the inner shield 701 is connected to the hub 725 to cover the non-patient end 734 of the needle 731.

A projection 704 extends outwardly from the base 703 of the inner shield 711. An opening is disposed in the base 703 and a passageway is disposed in the projection 704 to facilitate receiving the needle 731. The projection 704 of the inner shield 701 has a closed end 702 to cover the non-patient end 734 of the needle 731.

Figure 22:
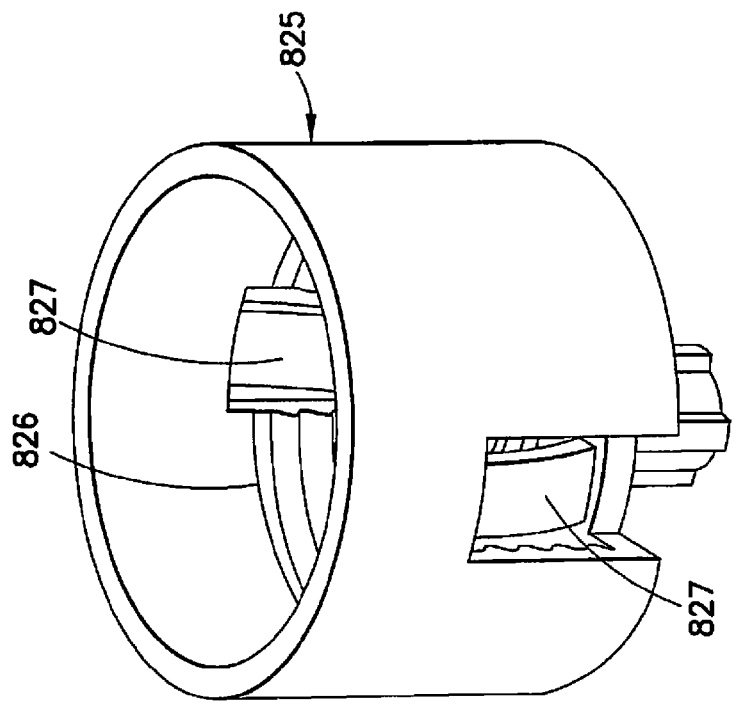
FIG. 22 is a perspective view of a hub having flexible arms adapted to receive the inner shield of FIG. 21.
Figure 21:
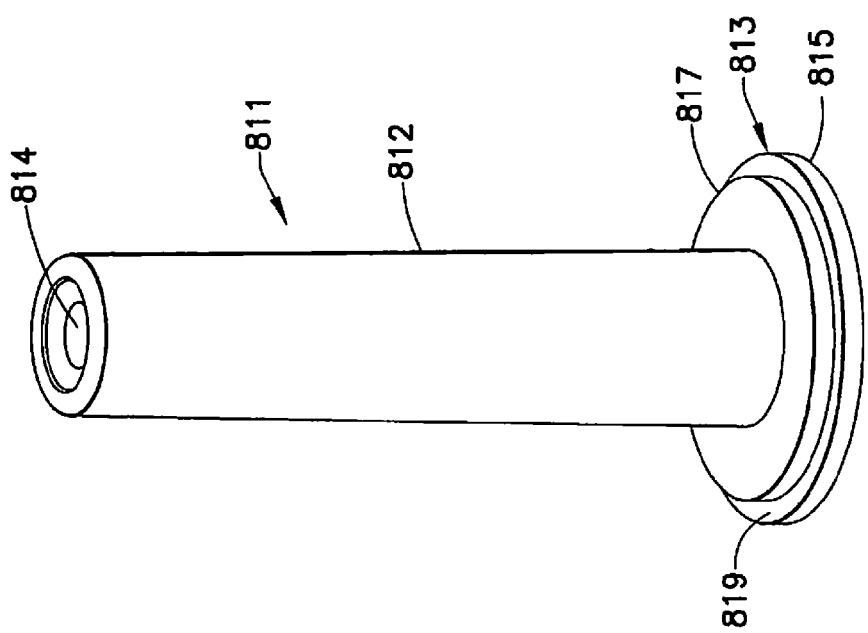
FIG. 21 is a perspective view of an inner shield having a stepped base according to another exemplary embodiment of the present invention.
Figure 23:
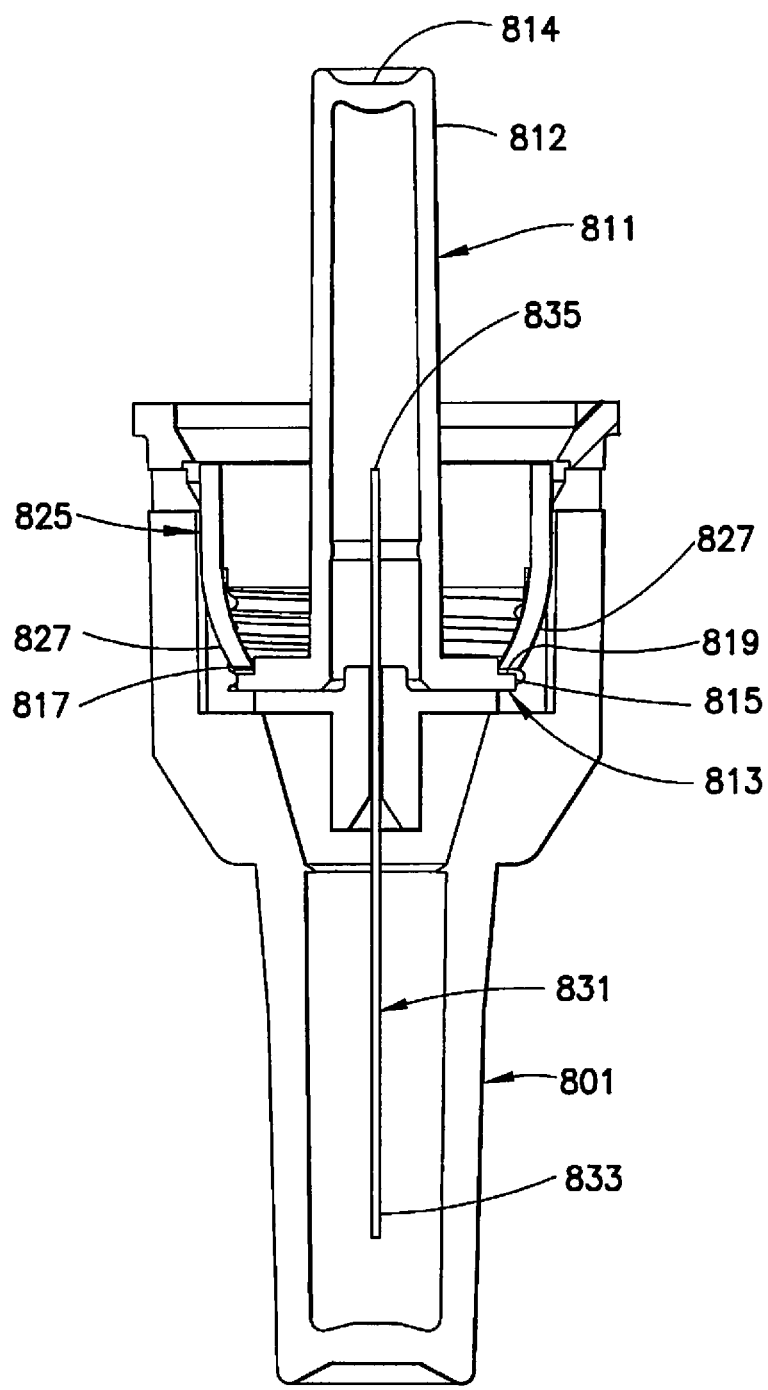
FIG. 23 is an elevational view in partial cross section of the inner shield of FIG. 21 connected to the hub of FIG. 22 to shield a non-patient end of a needle.

In another exemplary embodiment as shown in FIGS. 21-23, an inner shield 811 has a stepped base 813. The stepped base has a first portion 815 and a second portion 817, such that the second portion 817 has a smaller outer diameter than the first portion 815, as shown in FIG. 21. A projection 812 extends upwardly from the base 813 and has a closed end 814 to cover a non-patient end 835 of a needle 831. An opening is disposed in the base 813 and a passageway is disposed in the projection 812 to receive the needle 831, as shown in FIG. 23.

A hub 825, as shown in FIG. 22, has a pair of inwardly extending flexible arms 827. Preferably, the flexible arms 827 are diametrically opposed. The needle 831 is rigidly received by the hub 825, as shown in FIG. 23. Threads 826 allow the hub 825 to be threadably connected to a lower housing 17 of a drug delivery device 100.

The inner shield 811 is inserted in the hub 825, as shown in FIG. 23, to cover the non-patient end 835 of the needle 831. The first portion 815 of the stepped base 813 of the inner shield 811 flexes the arms 827 of the hub 825 outwardly as the inner shield is inserted in the hub. When the first portion 815 of the stepped base 813 passes the arms 827, the arms 827 flex back to their initial position and engage the shoulder 819 formed between the first and second portions of the base. The larger outer diameter of the first portion 815 of the stepped base 813 prevents the inner shield 811 from being withdrawn from the hub 825. Thus, the outer cover 801 protects the patient end 833 of the needle 831 and the inner shield 811 protects the non-patient end 835 of the needle 831. A user may manually flex the arms 827 outwardly to withdraw the inner shield 811 from the hub 825.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

What is claimed is:

1. A needle assembly, comprising:
   a hub including a flange;
   a needle fixedly connected to said hub;
   an opaque inner cover removably connected to said hub for covering said needle;
   a translucent outer cover for removably receiving said inner cover, said hub and said needle, said outer cover including an undercut; and
   a color indicator visible only when said inner cover is disconnected from said hub, wherein
   said flange is locked to said undercut only when said inner cover is disconnected from said hub.

2. The needle assembly according to claim 1, wherein said color indicator comprises a glue well of said hub.

3. The needle assembly of claim 1, wherein said opaque inner cover further comprises:
   an inner cover cavity for receiving a portion of said hub; and
   a base member surrounding said inner cover cavity, said base member configured to limit a depth of insertion of said hub within said outer cover cavity when said opaque inner cover is connected to said hub.

4. The needle assembly of claim 1, wherein:
   for use of said needle of said hub, said translucent outer cover is configured to be removed from said opaque inner cover and said opaque inner cover is configured to be removed from said hub; and
   after use of said needle of said hub, said translucent outer cover is further configured to be connected to said hub.

5. The needle assembly of claim 4, wherein:
   said color indicator is configured to be visually obscured by said opaque inner cover when said opaque inner cover is connected to said hub; and
   said color indicator is configured to be visually displayed by said translucent outer cover when said translucent outer cover is connected to said hub.

6. The needle assembly of claim 1, wherein said translucent outer cover further comprises:
   an outer cover cavity for receiving said opaque inner cover and for receiving said hub; and
   a flexible member disposed in said outer cover cavity, said flexible member configured to secure said hub within said outer cover cavity when said translucent outer cover is connected to said hub.

7. The needle assembly of claim 6, wherein said hub comprises a flange, said flange configured to be secured by said flexible member of said translucent outer cover.

8. A needle assembly, comprising:
   an opaque inner cover, configured to be removably connected to a needle hub; and
   a translucent outer cover, configured to be removably connected to said opaque inner cover;
   wherein said needle hub has a visible indicator comprising a colored glue well, said colored glue well being of a different color than a remaining portion of the needle hub;
   wherein said opaque inner cover is further configured to visually obscure said visible indicator of said needle hub when said opaque inner cover is connected to said needle hub; and
   wherein said translucent outer cover is further configured to visually display said visible indicator of said needle hub when said opaque inner cover is disconnected from said needle hub and said translucent outer cover is connected to said needle hub.

9. The needle assembly of claim 8, wherein said colored glue well is red.

10. The needle assembly of claim 8, wherein:
    for use of said needle hub, said translucent outer cover is further configured to be removed from said opaque inner cover and said opaque inner cover is further configured to be removed from said needle hub; and
    after use of said needle hub, said translucent outer cover is further configured to be connected to said needle hub.

11. The needle assembly of claim 10, wherein said opaque inner cover further comprises:
    an inner cover cavity for receiving a portion of said needle hub; and
    a base member surrounding said inner cover cavity, said base member configured to limit a depth of insertion of said needle hub within said outer cover cavity when said opaque inner cover is connected to said needle hub.

12. The needle assembly of claim 10, wherein said translucent outer cover further comprises:
   an outer cover cavity for receiving said opaque inner cover and for receiving said needle hub; and
   a flexible member disposed in said outer cover cavity, said flexible member configured to secure said needle hub within said outer cover cavity when said translucent outer cover is connected to said needle hub.

13. The needle assembly of claim 12, wherein said needle hub comprises a flange, said flange configured to be secured by said flexible member of said translucent outer cover.

14. A method of preventing reuse of a needle of a needle assembly for use with a drug delivery device, comprising the steps of:
   observing a visible indicator of a needle hub when contained within at least one of a translucent outer cover and an opaque inner cover, said translucent outer cover configured to be removably connected to said opaque inner cover, said visible indicator of said needle hub being visually obscured by said opaque inner cover when said opaque inner cover is connected to said needle hub, and said visible indicator of said needle hub being visually displayed by said translucent outer cover when said translucent outer cover is connected to said needle hub and when said opaque inner cover is disconnected from said needle hub, said visible indicator comprising a colored glue well, said colored glue well being of a different color than a remaining portion of the needle hub;
   if said visible indicator of said needle hub is visually displayed by said translucent outer cover, discarding said needle hub; and
   if said visible indicator of said needle hub is visually obscured by said opaque inner cover and said translucent outer cover, preparing said needle hub for use.

15. The method of claim 14, further comprising:
   returning said needle hub after use to said translucent outer cover, such that said visible indicator of said needle hub is visually displayed by said translucent outer cover.

* * * * *